United States Patent [19]

Alper et al.

[11] Patent Number: 4,634,780

[45] Date of Patent: Jan. 6, 1987

[54] PROCESS FOR THE PRODUCTION OF LACTONES

[75] Inventors: Howard Alper, Ottawa, Canada; David J. H. Smith, Camberley, England

[73] Assignee: The British Petroleum Company p.l.c., London, England

[21] Appl. No.: 779,784

[22] Filed: Sep. 24, 1985

[30] Foreign Application Priority Data

Sep. 27, 1984 [GB] United Kingdom ............... 8424376

[51] Int. Cl.$^4$ ............................................. C07D 309/30
[52] U.S. Cl. ..................................... 549/273; 549/295
[58] Field of Search ................................ 549/295, 273

[56] References Cited

U.S. PATENT DOCUMENTS 4,235,744 11/1980 Pesa et al. ........................... 549/295
4,451,407 5/1984 Pesa et al. ........................... 549/295

FOREIGN PATENT DOCUMENTS 105704 4/1984 European Pat. Off. .

Primary Examiner—Norma S. Milestone
Attorney, Agent, or Firm—Brooks Haidt

[57] ABSTRACT

Lactones are produced by reacting an unsaturated alcohol capable of intramolecular esterification to form a lactone ring with carbon monoxide in the presence of a protonic acid and a catalyst comprising (a) at least one of the metals palladium, rhodium, ruthenium, iridium and cobalt, and (b) at least one of the metals copper, molybdenum and iron, the metals (a) and (b) being in the form of either the elemental metal or a compound thereof.

12 Claims, No Drawings

PROCESS FOR THE PRODUCTION OF LACTONES

The present invention relates to a process for the production of lactones by the catalysed reaction of an unsaturated alcohol with carbon monoxide, optionally in the presence of oxygen.

Lactones are cyclic esters. gamma-Butyrolactone, for example, is manufactured by the oxidation of tetramethylene glycol over a copper catalyst and is an important intermediate in the preparation of polyamides.

Processes for the production of carboxylic acid esters by reacting an olefin with carbon monoxide and an alcohol in the presence of a catalyst and in the presence or absence of oxygen are known. Representative of the published art are U.S. Pat. No. 4,303,589, Belgian Pat. No. 877770, Japanese Patent Publication No. 53040709 and U.S. Pat. No. 3,780,074.

U.S. Pat. No. 4,303,589 (Monsanto) describes a process for the production of carboxylate esters by (a) reacting internal olefins with carbon monoxide and an alcohol at 170° to 200° C. and 1200–1800 psig in the presence of a cobalt catalyst and a pyridine promoter, (b) diluting the reaction mixture with a large amount of hydrocarbon to cause phase separation, (c) separating the ester from the other phase, which contains more than 90% of the cobalt catalyst and (d) recycling the catalyst to step (a).

Belgian Pat. No. 877770 describes the production of polycarboxylic esters by reacting an olefin containing at least two conjugated double bonds with carbon monoxide and an alcohol in the presence of a base and a palladium/copper catalyst.

Japanese Patent Publication No. 53040709 describes the production of dicarboxylic acid diesters by reacting an olefin, carbon monoxide, oxygen and an alcohol in the presence of a catalyst containing (a) a palladium group metal or a compound thereof, (b) a copper salt and (c) a tertiary amine.

Finally U.S. Pat. No. 3,780,075 describes the production of alkadienoic acid esters by reacting a 4–12 carbon acyclic conjugated aliphatic diolefin with a 1 to 20 carbon monohydroxy alcohol and carbon monoxide in the presence of zerovalent palladium and a phosphine activator at 80° to 160° C. in the absence of oxygen.

Methods are also known for the hydroesterification of acetylene to produce isomeric esters. For example, G. P. Chiusli et al report in Chem. Ind., 977, (1968) the reaction of acetylene with carbon monoxide in the presence of 4% oxygen and thiourea and a palladium (II) chloride catalyst. A disadvantage of this process is that the selectivity to isomeric esters (cis and trans-esters) is considerably reduced by the accompanying formation of polymeric materials and isomeric muconate esters.

Our copending European application publication No. 105704 discloses a process for the production of a carboxylic acid ester which comprises reacting an unsaturated hydrocarbon with carbon monoxide and an alcohol in the presence of a protonic acid and as a catalyst (a) at least one of the metals palladium, rhodium, ruthenium, iridium and cobalt, and (b) copper.

We have found that lactones can be produced by replacing the unsaturated hydrocarbon and the alcohol in the process of European application publication No. 105704 by an unsaturated alcohol.

Accordingly, the present invention provides a process for the production of a lactone which process comprises reacting an unsaturated alcohol capable of intramolecular esterification to form a lactone ring with carbon monoxide in the presence of a protonic acid and a catalyst comprising (a) at least one of the metals palladium, rhodium, ruthenium, iridium and cobalt, and (b) at least one of the metals copper, molybdenum and iron, the metals (a) and (b) being in the form of either the elemental metal or a compound thereof.

The process of the invention offers an alternative route for the synthesis of lactones and one, moreover, which can be operated under remarkably mild temperature and pressure conditions.

As regards the unsaturated alcohol, there may be used any unsaturated alcohol which is capable, under the conditions of the process, for intramolecular esterification to form a lactone ring. Suitable alcohols are those having the formula ROH wherein R is either an olefinically unsaturated or acetylenically unsaturated hydrocarbyl group. Generally, unsaturated alcohols capable of forming 5-, 6- and 7-membered rings will be found most useful in the operation of the process. Preferably the unsaturated alcohol is an allylic alcohol which may be a primary, secondary or tertiary allylic alcohol. Examples of unsaturated alcohols which may be employed in the process of the present invention are allyl alcohol, 3-buten-1-ol, trans-2-buten-1-ol, 3-buten-2-ol, 2-methyl-2-propen-1-ol, 2-methyl-3-buten-1-ol, 2-methyl-3-buten-2-ol, 3-penten-2-ol, 4-penten-2-ol, 4-penten-1-ol, 1-hexen-3-ol, 5-hexen-2-ol, cis-3-hexen-1-ol, cis-2-hexen-1-ol and trans-2-hexen-1-ol.

The carbon monoxide may be provided by any suitable source. The carbon monoxide pressure may suitably be the autogenous pressure at the reaction temperature employed. Alternatively, elevated pressures, suitably in the range from 2 to 250 psig above the autogenous pressure at the reaction temperature may be employed.

The protonic acid may be either a mineral acid, preferably hydrochloric acid or sulphuric acid, or an organic acid which may suitably be a carboxylic acid.

With regard to the catalyst, one or more of the metals palladium, rhodium, ruthenium, iridium and cobalt is employed as component (a). The metal(s) may be in the form of the elemental metal(s), such as a finely divided powder, or in the form of a compound of the metal(s). Suitable compounds of the metal(s) include the chloride, iodides, acetates and nitrates, preferably the chlorides. Preferably the metal is palladium, suitably in the form of palladium (II) chloride.

One or more of the metals copper, molybdenum and iron is employed as component (b) of the catalysts. Preferably component (b) is copper.

Copper may suitably be added as a cuprous or a cupric compound or as a mixture thereof. A wide variety of copper compounds may be used in the process of the invention. Examples of suitable copper compounds include copper (I) acetate, copper (II) acetylacetonate, copper (I) bromide, copper (I) chloride, copper (II) chloride, copper (I) iodide, copper (II) nitrate, and the like.

As regards the ratios of the catalyst components, the molar ratio of copper component (b) to metal(s) component (a) may suitably be in the range from 1:1 to 200:1, preferably from 2:1 to 50:1.

The molar ratio of unsaturated alcohol to the metal(s) component (a) may suitably be in the range from 5:1 to 1000:1, preferably from 10:1 to 250:1.

Oxygen may be present or absent. However, it is preferred to operate in the presence of oxygen because by doing so the product yields can be improved. Oxygen may be supplied to the reaction either as essentially pure oxygen or admixed with other gases which are substantially inert under the reaction conditions. Air may conveniently be used as the source of oxygen. The oxygen pressure may suitably be the autogenous pressure at the reaction temperature employed. Alternatively elevated pressures may be employed if desired.

A supplemental solvent may be employed if desired. The particular solvent employed may form a single phase with the unsaturated alcohol reactant. Alternatively, a solvent which is capable of forming a second liquid phase may be employed. The particular solvent employed should be inert under the reaction conditions. Suitable solvents which form a single phase with the alcohol reactant include oxygenated hydrocarbons, for example tetrahydrofuran. Polyalkylene glycols, for example polyethylene glycol, may also be used as the oxygenated hydrocarbon solvent. Suitable solvents capable of forming a second liquid phase include aliphatic hydrocarbons, cycloaliphatic hydrocarbons, aromatic hydrocarbons, alkyl-substituted aromatic hydrocarbons or halogenated aliphatic or aromatic hydrocarbons. Examples of suitable solvents capable of forming a second liquid phase include benzene, toluene, hexane, cyclohexane, chlorobenzene, bromobenzene, a xylene, dichloromethane, chloroform and 1,2-dichloroethane. It will be appreciated by those skilled in the art that the organic solvent should be chosen having regard to the difference in boiling points between the products of the reaction and the solvent so as to facilitate separation of the reaction mixture into its individual components. The amount of supplemental solvent based on the unsaturated alcohol reactant may vary over a wide range, suitably from 20 to 0.2, preferably from 5 to 1, volumes of supplemental solvent per volume of unsaturated alcohol reactant.

Using solvents which are capable of forming a second liquid phase it may be advantageous to employ a surfactant. Typical of the surfactants which may be used are quaternary ammonium salts, for example cetyltrimethylammonium bromide, alkali metal sulphates, alkali metal salts of alkaryl sulphonic acids, alkali metal salts of alkanoic acids and 1-alkyl pyridinium salts.

The process may be suitably be operated at ambient temperature, though elevated temperatures, for example in the range 20° to 150° C. or even higher may be employed. The reaction time may vary over a wide range, suitably from about 30 minutes to 8 hours, though longer reaction times may be employed if desired.

The process may be carried out batchwise or continously, preferably continously.

The invention will now be described in greater detail by reference to the following Examples.

PROCESS OPERATED IN THE PRESENCE OF OXYGEN

Example 1

Carbon monoxide (1atm.) was bubbled through dry tetrahydrofuran (65 ml) at room temperature. Palladium (II) chloride (0.14 g; 0.78 mmol) was then added, followed by HCl (0.5 ml) and copper (II) chloride (0.84 g). Oxygen bubbling was commenced and 3-buten-1-ol (7.8 mmol) was added. The reaction mixture was stirred overnight at room temperature, filtered and the filtrate distilled.

alpha-Methylbutyrolactone was obtained in 80% yield.

Example 2

Example 1 was repeated except that 2-methyl-3-buten-1-ol was used in place of 3-buten-1-ol and only 0.21 g copper (II) chloride was used.

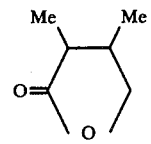

was obtained in 50% yield.

Example 3

Example 2 was repeated except that copper (II) acetate was used in place of copper (II) chloride.

The same lactone product was obtained in substantially the same yield.

Example 4

Example 2 was repeated except that 4-penten-2-ol was used in place of 2-methyl-3-buten-1-ol.

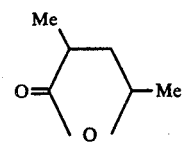

was obtained in 75% yield.

Example 5

Example 1 was repeated except that 4-penten-1-ol was used in place of 3-buten-1-ol.

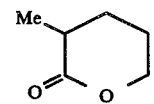

was obtained in 40% yield.

Example 6

Example 2 was repeated except that 5-hexen-2-ol was used in place of 2-methyl-3-buten-1-ol.

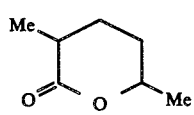

was obtained in 46% yield.

Example 7

Example 2 was repeated except that allyl alcohol was used in place of 2-methyl-3-buten-1-ol.

Gamma-butyrolactone was obtained in 34% yield.

Example 8

Example 2 was repeated except that trans-2-buten-1-ol was used in place of 2-methyl-3-buten-1-ol.

Alpha-methyl-gamma-butyrolactone was obtained in 50% yield.

Example 9

Example 2 was repeated except that 3-buten-2-ol was used in place of 2-methyl-3-buten-1-ol.

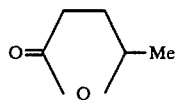

was obtained in 70% yield.

Example 10

Example 2 was repeated except that 2-methyl-2-propen-1-ol was used in place of 2-methyl-3-buten-1-ol.

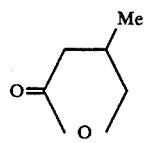

was obtained in 15% yield.

Example 11

Example 2 was repeated except that 2-methyl-3-buten-2-ol was used in place of 2-methyl-3-buten-1-ol.

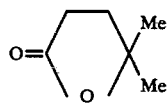

was obtained in 42% yield.

Example 12

Example 2 was repeated except that 3-penten-2-ol was used in place of 2-methyl-3-buten-1-ol.

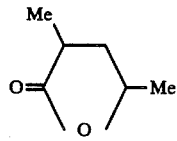

was obtained in 54% yield.

Example 13

Example 2 was repeated except that 1-hexen-3-ol was used in place of 2-methyl-3-buten-1-ol.

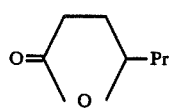

was obtained in 40% yield.

Example 14

Example 2 was repeated except that cis-2-hexen-1-ol was used in place of 2-methyl-3-buten-1-ol.

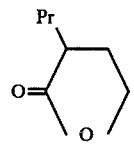

was obtained in 63% yield.

Example 15

Example 2 was repeated except that trans-2-hexen-1-ol was used in place of 2-methyl-3-buten-1-ol.

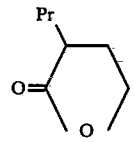

was obtained in 25% yield.

We claim:

1. A process for the production of a lactone which process comprises
reacting an unsaturated alcohol having the formula ROH wherein R is an olefinically unsaturated hydrocarbyl group in which the olefinic unsaturation is not more than three carbon atoms removed from the hydroxy substituent and said unsaturated alcohol being capable of intramolecular esterification to form a 5- or a 6-membered lactone ring,
with carbon monoxide in the presence of a protonic acid and a catalyst comprising (a) at least one of the metals palladium, rhodium, ruthenium, iridium and cobalt, and (b) at least one of the metals copper, molybdenum and iron, the metals (a) and (b) being in the form of either the elemental metal or a compound thereof.

2. A process according to claim 1 wherein the unsaturated alcohol is either a primary, a secondary or a tertiary allylic alcohol.

3. A process according to claim 1 wherein the protonic acid is either a mineral acid or an organic acid.

4. A process according to claim 1 wherein the component (a) of the catalyst is palladium.

5. A process according to claim 1 wherein the component (b) of the catalyst is copper.

6. A process according to claim 1 wherein an oxygenated hydrocarbon is employed as a supplemental solvent.

7. A process according to claim 1 wherein the reaction is effected at ambient temperature.

8. A process according to claim 1 wherein the reaction is effected at a temperature in the range 20° to 150° C.

9. A process according to claim 1, wherein the reaction is carried out in the presence of oxygen.

10. A process according to claim 1, wherein the unsaturated alcohol is selected from the group consisting of 3-buten-1-ol, trans-2-buten-1-ol, 3-buten-2-ol, 2-methyl-2-propen-1-ol, 2-methyl-3-buten-1-ol, 2-methyl-3-buten-2-ol, 3-penten-2-ol, 4-penten-2-ol, 4-penten-1-ol, 1-hexen-3-ol, 5-hexen-2-ol, cis-3-hexen-1-ol, cis-2-hexen-1-ol and trans-2-hexen-1-ol.

11. A process according to claim 1, wherein the catalyst component (a) is at least one of the metals palladium rhodium and iridium, or a compound thereof.

12. A process for the production of a lactone which process comprises reacting an unsaturated alcohol having the formula ROH wherein R is an olefinically unsaturated hydrocarbyl group, in which the olefinic unsaturation is not more than three carbon atoms removed from the hydroxy substituent and said unsaturated alcohol being capable of intramolecular esterification to form a 5- or a 6-membered lactone ring, said unsaturated alcohol being selected from the group consisting of 3-buten-1-ol, trans-2-buten-1-ol, 3-buten-2-ol, 2-methyl-2-propen-1-ol, 2-methyl-3-buten-1-ol, 2-methyl-3-buten-2-ol, 3-penten-2-ol, 4-penten-2-ol, 4-penten-1-ol, 1-hexen-3-ol, 5-hexen-2-ol, cis-3-hexen-1-ol, cis-2-hexen-1-ol and trans-2-hexen-1-ol, with carbon monoxide in the presence of a protonic acid and a catalyst comprising (a) at least one of the metals palladium, rhodium, and iridium, and (b) at least one of the metals copper, molybdenum and iron, the metals (a) and (b) being in the form of either the elemental metal or a compound thereof, and said reaction being carried out in the presence of oxygen.

* * * * *